United States Patent
Perrier (10) Patent No.: US 7,909,782 B2
(45) Date of Patent: Mar. 22, 2011

(54) ULTRASONIC MEDICAL DEVICE

(75) Inventor: John Perrier, Brisbane (AU)

(73) Assignee: John Perrier, Brisbane (AU)

( * ) Notice: Subject to any disclaimer, the term of this patent is extended or adjusted under 35 U.S.C. 154(b) by 480 days.

(21) Appl. No.: 12/071,193

(22) Filed: Feb. 19, 2008

(65) Prior Publication Data

US 2008/0139972 A1    Jun. 12, 2008

Related U.S. Application Data (63) Continuation-in-part of application No. 10/532,210, filed on Apr. 22, 2005, now abandoned.

(51) Int. Cl.
*A61N 7/00* (2006.01)

(52) U.S. Cl. ............................................................ 601/2

(58) Field of Classification Search ............... 601/1–3; 600/9–15, 437, 446, 427, 350, 491; 128/774; 325/15–22
See application file for complete search history.

(56) References Cited

U.S. PATENT DOCUMENTS

| | | | |
|---|---|---|---|
| 5,086,788 A * | 2/1992 | Castel et al. | 607/150 |
| 5,269,747 A | 12/1993 | Erickson | |
| 5,549,544 A | 8/1996 | Young | |
| 5,857,957 A | 1/1999 | Lin | |
| 5,976,091 A * | 11/1999 | Hanafy | 600/459 |
| 6,007,499 A * | 12/1999 | Martin et al. | 601/3 |
| 6,058,932 A * | 5/2000 | Hughes | 128/200.24 |
| 6,355,006 B1 | 3/2002 | Ryaby | |
| 6,419,648 B1 * | 7/2002 | Vitek et al. | 601/3 |
| 6,506,154 B1 * | 1/2003 | Ezion et al. | 600/437 |
| 6,585,649 B1 * | 7/2003 | Mendlein et al. | 600/438 |
| 2003/0069526 A1 * | 4/2003 | Thompson et al. | 601/2 |
| 2004/0006272 A1 * | 1/2004 | Vortman et al. | 600/443 |
| 2005/0197576 A1 * | 9/2005 | Luo et al. | 600/438 |

FOREIGN PATENT DOCUMENTS

| | | |
|---|---|---|
| GB | 1500072 | 2/1978 |
| JP | 2002 000613 | 1/2002 |
| RU | 2208429 | 7/2003 |
| WO | WO 98/07373 A1 | 2/1998 |
| WO | WO 0122897 | 4/2001 |

* cited by examiner

*Primary Examiner* — Eric F Winakur
*Assistant Examiner* — Lawrence N Laryea
(74) *Attorney, Agent, or Firm* — Stein McEwen, LLP (57) ABSTRACT

Ultrasonic medical apparatus is disclosed comprising ultrasonic transducers and associated electronics incorporated in a portable hand-held device adapted for engagement with the neck of a person and energized to induce a coughing reflex in the person. The apparatus can be utilized on subjects who, for various reasons, are unable to initiate coughing themselves at the time, and results in the effective clearing of fluid and debris within small airways in the lungs which cannot be reached by intrusive suction clearing.

19 Claims, 5 Drawing Sheets

ULTRASONIC MEDICAL DEVICE

RELATED APPLICATION

This is a continuation in part of U.S. application Ser. No. 10/532,210, filed Apr. 22, 2005 now abandoned.

BACKGROUND OF THE INVENTION

This invention relates to medical apparatus for the induction of reflexive responses in a patient. It has particular but not exclusive application to inducing a coughing reflex in human patients, and for illustrative purposes, reference will be made to such application. However, it is to be understood that the apparatus may be used in other applications, such as inducing other reflexive responses and/or similar responses in animals.

It is well known that the coughing reflex is a vital part of maintaining normal lung function, as it acts to rid the lungs of excessive secretions such as mucus or inhaled substances. In some cases, human patients and animals are unable to cough on demand, rendering them liable to the exacerbation or prolongation of respiratory problems.

Those people who are unable to cough on demand include the very young, gravely ill and incapacitated patients, unconscious or heavily sedated patients, patients who have undergone a near-drowning experience or overdosed on drugs which have suppressed their central nervous system, victims of stroke, elderly patients who have lost control of their bodily functions, intubated and incubated patients with temporary airways such as those in intensive care situations and patients who are anaesthetised during or immediately post surgery. Such conditions also exist in the veterinary context for animals.

Prior art methods of clearing the upper respiratory tract of mucous or to induce a coughing reflex is usually through the introduction by intubation of the upper airway tract such as vacuum drainage or pulmonary lavage catheters. The problem with the introduction of such devices is that this is an artificial and largely inefficient method to clear mucus or other secretions blocking the lower respiratory airways. To be precise, it does not have the benefit of the explosive clearing mechanism normally associated with a coughing spasm. Furthermore, while the upper respiratory tract may be cleared by suction, smaller airways, such as the bronchi and bronchioles cannot be so easily cleared.

Every year, tens of thousands of people die because of respiratory problems. Foremost among these deaths are sufferers of the following conditions:
  respiratory illness;
  bronchitis (acute and chronic);
  pneumonia;
  chest infections (bacterial and microbial);
  pediatric respiratory problems;
  cystic fibrosis;
  bronchiolitis (a pediatric form of bronchitis);
  bums injuries;
  drowning, and
  self-aspiration, for example after a drug or alcohol overdose.

Many of these people die because their lungs fill with excessive secretions or fluids. The usual method of self-clearing the lungs is to cough. However, huge sections of the population are unable to cough effectively, rendering them vulnerable to respiratory problems and premature death.

Even in a hospital environment, the method of clearing the chest of such patients are ineffective. Usually, a suction catheter is used to draw the secretions out of the lungs. One major problem with this method is that only the very uppermost airways are cleared. As the catheter cannot penetrate to the mid or lower airways, almost all of the secretions stay put. Pneumonia and chest infections are frequent sequelae.

Furthermore, a suction catheter is not readily transportable outside a hospital—for example, to a beach, a park or a nursing home. The only truly effective way to clear the lower airways of the lungs is of course to cough.

Medical staff have tried many techniques over the years to stimulate the all-important coughing reflex Methods have included manual pressure to the front of the neck, blowing dry oxygen down the throat, and tickling the back of the palate with a catheter. None of these methods has proved reliably effective. The catheter-tickling method can sometimes even be dangerous as the patient can gag and then aspirate the vomitus. In short, no simple method currently exists to stimulate an all-important coughing reflex The coughing reflex is therefore a natural mechanism wherein air is expelled under force which clears the pulmonary system from the smallest airway towards the trachea. The situation is even more acute with heavily sedated or unconscious patients or animals wherein the smaller airways are blocked and cannot be cleared by the introduction of suction tubes. Respiration can be compromised to the extent where the respiratory centre is completely depressed through hypoxia and the patient or animal eventually dies from asphyxiation, infection or pneumonia.

SUMMARY OF THE INVENTION

It is the therefore an object of the present invention to seek to alleviate or ameliorate some of the limitations and disadvantages of the prior art or to at least provide the public with a useful choice.

In one aspect, this invention resides in coughing reflex inducing apparatus for inducing a coughing reflex in a person or animal, said apparatus including:
  ultrasonic wave generation means for producing ultrasonic vibrations of a frequency suitable for at least limited penetration of soft body tissue, whereby application of said generation means to a suitable contact region on the body of the person may stimulate a reflexive response.

Suitably, the ultrasonic wave generation means includes an ultrasonic transducer adapted for producing mechanical vibrations in response to vibratory electrical input from an electrical oscillator. However, if desired, other generating means, such as fluidics transducers and oscillators, which function by producing pressure oscillations in a gas, may be used. The ultrasonic transducer suitably comprises a piezo-electric transducer and preferably a piezo-ceramic electric transducer.

A single ultrasonic transducer may be utilised. However it is preferred that a transducer array of at least two transducers be provided and that the transducers forming said array are held in positions and orientations which maximise contact with the region known to stimulate the desired response. In order to enhance such contact, the transducers may be mounted flexibly relative to one another, being disposed along a flexible mount and/or being attached to a mount through flexible mountings. The flexible mounting may comprise a spring mounting for the transducers that permits the apparatus to adjust automatically to the neck of a person or animal to which the apparatus is applied with the spring mounted transducers retracting for necks of larger size. The transducers are suitably angled to each other to ensure correct penetration of the neck and most preferably the transducers have their active faces are angled at, and so as to emit ultrasonic waves at, 80 to 100 degrees to each other and most preferably approximately 90 degrees to each other. Adjustment means may be provided between transducers and the mount whereby the position of the transducers relative to one another may be optimised to suit a particular neck.

The transducer array may be mounted to a transducer support that forms an applicator head and the transducer support may be mounted to a handle. The handle may contain all or part of the electronic circuitry required to power the transducer array. The transducer support may be attached detachably to the handle, and a plurality of arrays or transducer supports may be provided for interchange, the arrays differing in size and/or array pattern to accommodate necks of differing size or shape. It is envisaged that much smaller arrays than normal may be required for pediatric applications. The transducer support may be of a concave configuration on one side to match the shape of a neck to which the transducer arrays are to be applied. The transducer support suitably extends symmetrically to opposite sides of the handle and the handle extends from the transducer support on the side of the support opposite the concave side.

The effective transfer of ultrasonic vibration into the neck is dependent on achieving good contact between the neck and the active faces of the transducers. In order to ensure that this is achieved, contact sensing means may be provided for determining the quality of the contact between the transducers and a neck, and contact indicating means indicate when good contact has been made. Suitably, this may be achieved with electronic circuitry adapted to drive the transducers at a low power level while sensing the damping of the oscillations which occurs when in good contact with the neck, and illuminating a light when good contact is achieved. If desired, individual lights may be provided for each transducer, allowing a user greater feedback for applying the apparatus correctly.

In a further aspect, this invention resides in a method of inducing a reflexive coughing response in a person or animal, including the steps of:

applying ultrasonic wave generation means externally to the neck or throat region of a person or animal, causing ultrasonic waves generated by the ultrasonic wave generation means to penetrate the soft tissue of the neck or throat region thereby eliciting a reflexive coughing response in the person or animal.

On application of the ultrasonic wave generation means to the external neck or throat region, the ultrasonic waves produced stimulate the back of the neck or the throat thereby facilitating the elicitation of a reflexive coughing response in the person or the animal.

Preferably the ultrasonic wave generation means is an ultrasonic transducer and preferably a piezo-electric transducer suitably of a ceramic material that produces ultrasonic waves when energized by electric current. The ultrasonic wave generation means suitably comprises an array of at least two transducers. Preferably the ultrasonic waves produced are of low intensity and within the safe power capabilities of current electrotherapeutic ultrasound apparatus.

The ultrasonic waves generated penetrate through the soft tissue of the neck or throat through to the pharynx or upper respiratory tract to stimulate a reflexive coughing response. Preferably the reflexive coughing response is due to the stimulation of the cilia which lines the pharynx.

Preferably the applicator head is designed to hold the piezo-ceramic transducers snugly to the patient's skin with minimal interference to any other therapy that may be used simultaneously. Alternatively the transducers may be covered with a resilient padding for example of foam plastics material for snug fit against the patient's neck.

As an alternative to the electronic circuitry being provided in the handle of the device, the part of the apparatus that delivers the electric signal to the piezo-ceramic transducers, thus causing them to vibrate, is housed in a separate housing which may comprise a moulded box-shaped housing of polyurethane or other similar material and the signal is applied to the device through a cable. Preferably the housing houses a printed circuit board and other electronic components that modulate the ultrasonic wave.

The applicator member or head in a further configuration may be of moulded form and adapted to fit snugly around the front of a patients or animals neck, just below the chin. The applicator member or head in this configuration may be in the form of an annular collar such as a split collar which may be split for location about the neck of a person or animal and then rejoined or reconnected. Preferably the applicator member or head in this embodiment houses at least two spaced ultrasound transducers which are spaced around to collar to ensures that the ultrasonic transducers are correctly positioned so as to direct the ultrasonic waves to the correct part of the patient's or animal's pharynx or upper respiratory tract to ensure that a cough is stimulated. Preferably the ultrasound parameters are pre-programmed in terms of specific wavelength, intensity, pulsation, wave form, time of application and number of pulses wherein the combination of parameters is the most effective at producing a cough reflex.

Preferably the delivery of the electrical signal to the piezo-ceramic transducers in the latter embodiment can be pre-programmed by a clinician to a protocol that is optimal for each particular patient and their presenting condition. Most preferably, the electrical signal is applied at regular intervals. For example, the clinician, therapist, doctor or nurse may program three coughs, 30 seconds apart, at hourly intervals. Alternatively they may program one cough every two hours for two days, then one cough every four hours on the following day. The automated cough stimulating device would then deliver the ultrasonic dose at the prescribed intervals, complementing the patient's respiratory treatment without the need for further intervention by staff. Preferably the clinician can use software-based controllers in the control unit to program any reasonable combination of period and frequency to stimulate the cough response. Preferably this cough response will then happen automatically without the presence of the clinician.

Preferably the power supply for the apparatus has battery level and power indicator light. Preferably the lights are light emitting diodes (LED) wherein a green LED will indicate that the device is in a ready mode. Preferably the green LED will turn red during the operation or application. Preferably there are skin contact indicators in the form of LED's that will turn red if poor contact is made with the patient's skin.

Preferably the device has a seamless construction to allow for outdoor and wet area usage and to allow for easy cleaning and sterilization.

The ultrasonic transducers in the above embodiments may be mounted on the applicator head or transducer support via a spring or resilient mounting so that contact is ensured even with the smallest neck wherein the spring mounted modules can retract for necks of larger sizes.

In another aspect, the present invention provides cough inducing apparatus for inducing a coughing reflex in a person or animal which includes an elongated main body having a first end and a second end and an applicator assembly. The applicator assembly comprises a transducer support having a concave side and spaced apart opposite free ends. The first end of the main body is connected to the transducer support on the side of the transducer opposite the concave side such that the main body extends from the first end away from the transducer support. The transducer support includes respective support arms extending symmetrically to opposite sides of the main body from the first end of the main body to the opposite free ends of the transducer support respectively.

A first ultrasonic transducer is supported on one transducer support arm and a second ultrasonic transducer is supported on the other transducer support arm such that the transducers are arranged at spaced apart positions along the transducer support and are angled towards each other and are adapted to be located at spaced regions around the neck of the person or animal. An ultrasonic wave generator is connectable to the ultrasonic transducers for producing ultrasonic vibrations in the transducers of a frequency suitable for at least limited penetration of soft body tissue of the neck and at said spaced regions of the neck to stimulate the upper respiratory tract of said person or animal and cause a reflexive coughing response in the person or animal.

BRIEF DESCRIPTION OF THE DRAWINGS

In order that the invention to be more readily understood and put into practical effect, reference will now be made to the accompanying diagrams, which illustrate preferred embodiments of the invention, wherein.

DETAILED DESCRIPTION OF THE PREFERRED EMBODIMENTS

Figure 1:
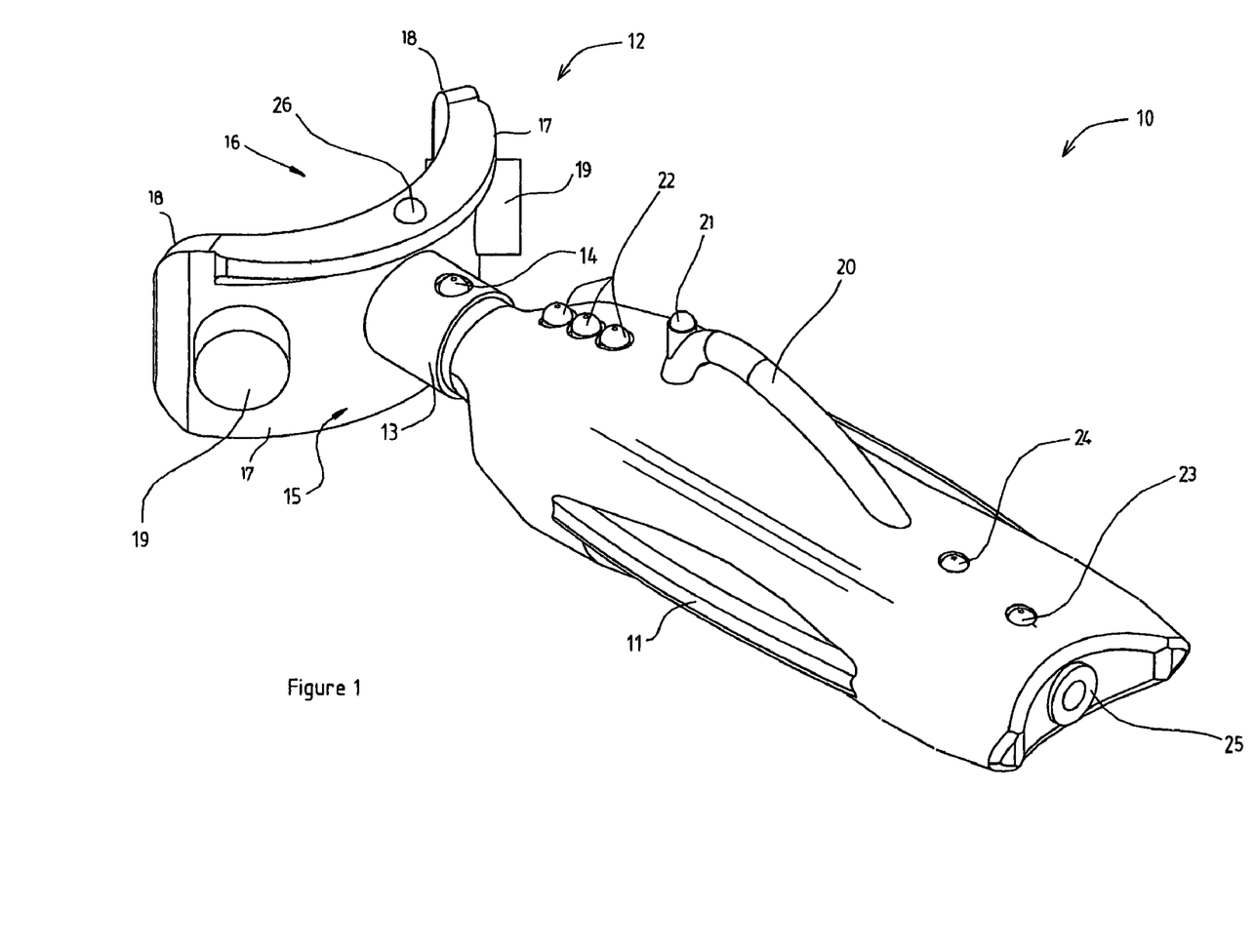
FIG. 1 is a perspective view of a coughing-reflex inducer apparatus according to the invention.
Figure 2:
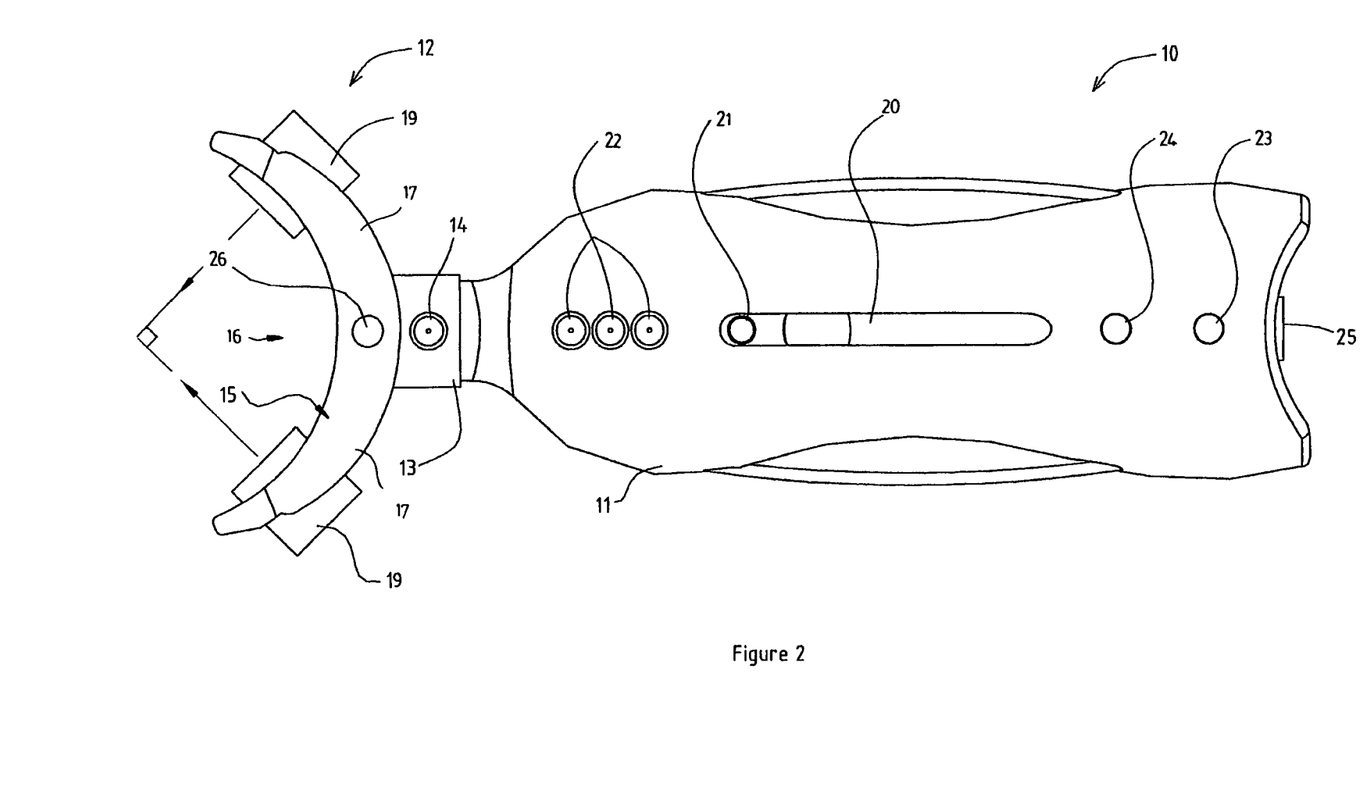
FIG. 2 is a top view of the apparatus shown in FIG. 1.
Figure 3:
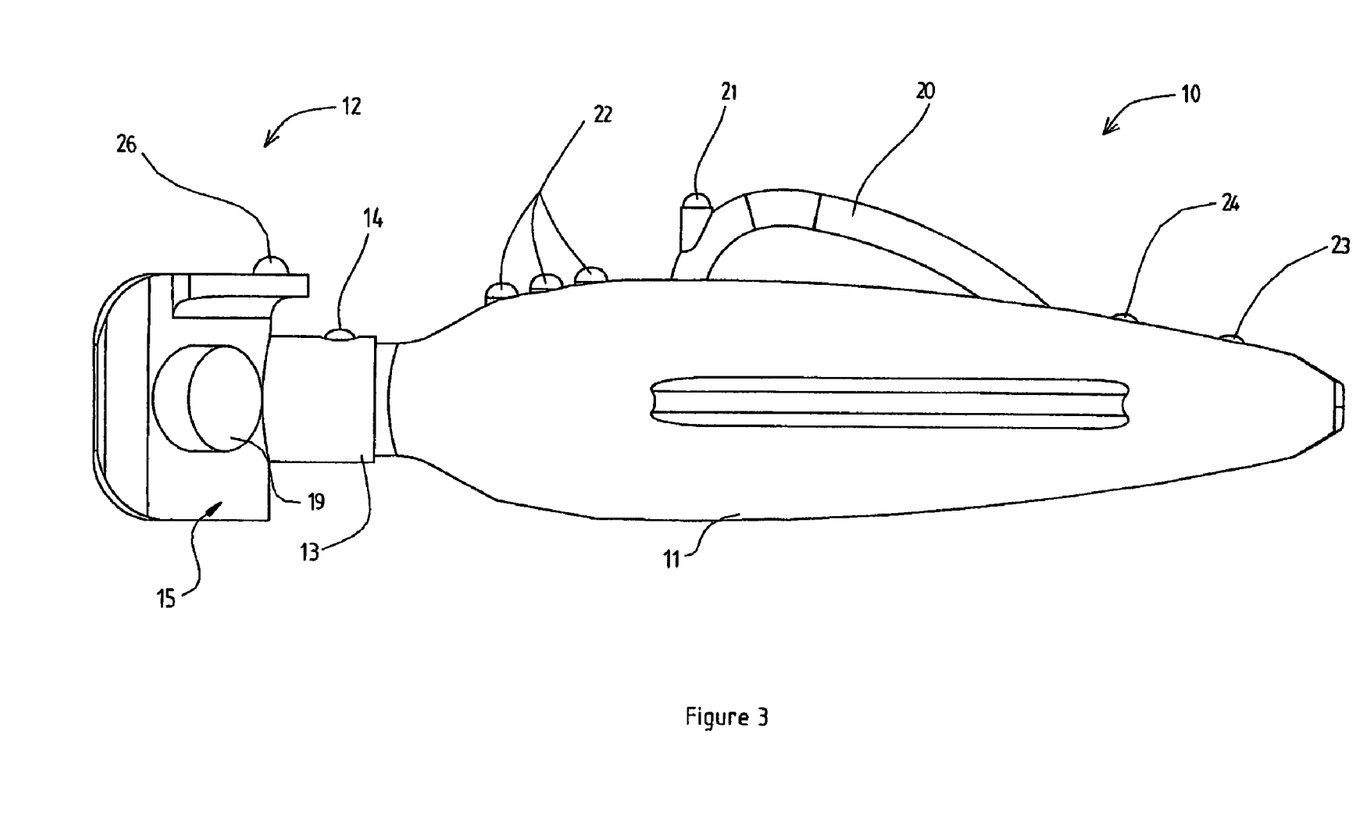
FIG. 3 is a side view of the apparatus shown in FIG. 1.

The coughing-reflex inducer 10 shown in FIGS. 1, 2 and 3 includes an elongated main body 11 and an applicator assembly 12 which is attached to one end of the main body 11 through a snap-on/off joint 13 and which is locked to the main body 11 by a detent button 14 which is depressed to release the applicator assembly 12 from the body 11. The applicator assembly 12 includes an arcuate transducer support 15 which extends symmetrically to opposite sides of the main body 11, the transducer support 15 having a concave operative side 16 for location against the external surface of the neck of a person or animal. The body 11 thus extends away from the transducer support 15 on the side of the support 11 opposite the concave side 16.

The transducer support 15 includes opposite arms 17 that extend symmetrically to opposite sides of the main body 15 and terminate in free ends 18 comprising the opposite ends of the transducer support 15. The transducer support 15 carries a pair of ultrasonic transducers 19 with respective transducers 19 being provided on the respective arms 17 to be arranged symmetrically relative to the body 11. The transducers 19 which comprise piezoelectric transducers are thus angled to each other typically at an angle of 90 degrees to each other as is apparent in FIG. 2 so that the ultrasonic waves are emitted thereby at approximately ninety degrees to each other.

The body 11 encloses a power electronic oscillator for supplying a signal to the transducers 19, batteries and timing equipment (not shown). The body 11 is supported on a gripping handle 20 which carries a two-stage actuation switch 21. The body 11 alternatively may itself comprise a gripping handle for manipulation of the inducer 10 in which case the handle 20 can be eliminated. A group of push-button switches 22 is provided on the body 11 for pre-setting treatment options such as intensity and duration of the ultrasonic treatment. A battery-indicator light 23 is provided to indicate the energy level of the battery, and a "power-on" indicator light 24 is provided which is illuminated whenever the apparatus is in operation. A charging socket 25 is provided for charging the internal rechargeable batteries (not shown). A "contact quality" indicator light 26 is provided on the support 15 to indicate when the transducers 19 are in effective contact with the neck.

In use, the inducer 10 is held by the handle 20 by the practitioner and presented to the neck of a patient with the surfaces of the transducers 19 in contact with the neck. If a good fit to the shape of the neck cannot be obtained, the applicator assembly 12 is detached from the body 11 at the joint 13 and another applicator assembly 12 with different geometry is attached. The practitioner makes appropriate adjustments to the settings of the push-buttons 22, then presses the first stage of the actuation switch 21. This initiates low-powered ultrasonic emanations from the transducers 19 and if the degree of damping measured by the electronic circuitry is sufficient to indicate good contact between the transducers 19 and the neck, the light 26 illuminates. If the light 26 does not illuminate, the practitioner must re-align the transducers 19 with the neck until it does. The practitioner can then press the second stage of the actuation switch 21, and higher-power ultrasonic waves generated by the apparatus penetrate the neck tissues, and the vibrations excite the hair-like structures known as cilia that line the pharynx. It is believed that this excitation simulates the effect on the cilia of ingested dust or debris, and the coughing reflex is induced as if to clear such dust or debris. In addition, the ultrasonic waves emitted by both transducers 19 being applied to spaced regions of the neck tend to insect or meet in the region of the cilia at the level of the oro-pharynx thus producing an effective cough response.

Figure 4:
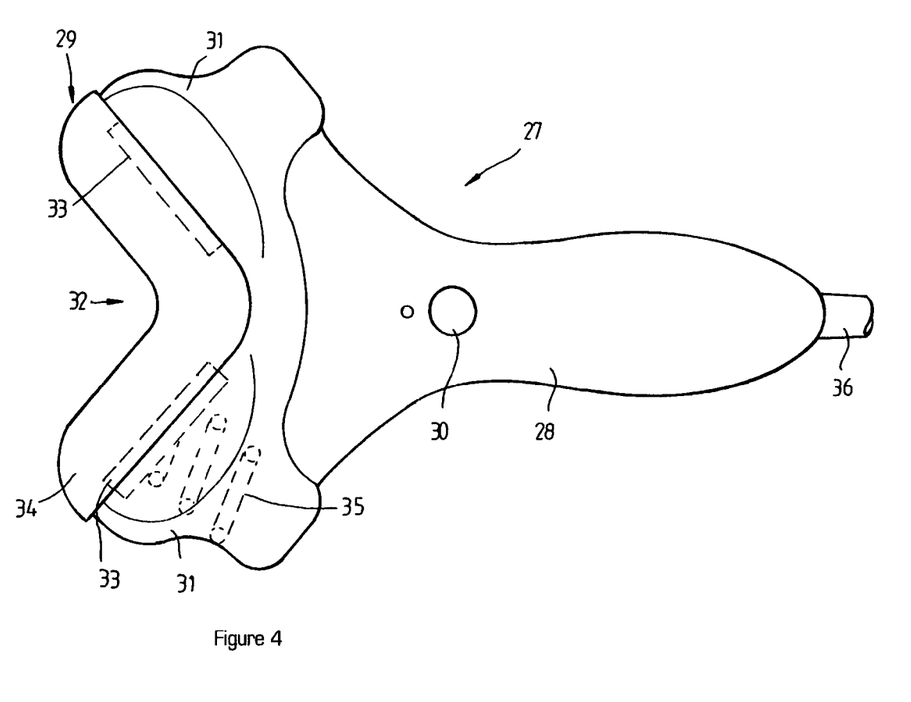
FIG. 4 is a top view of an alternative embodiment of coughing-reflex inducer apparatus according to the invention.
Figure 5:
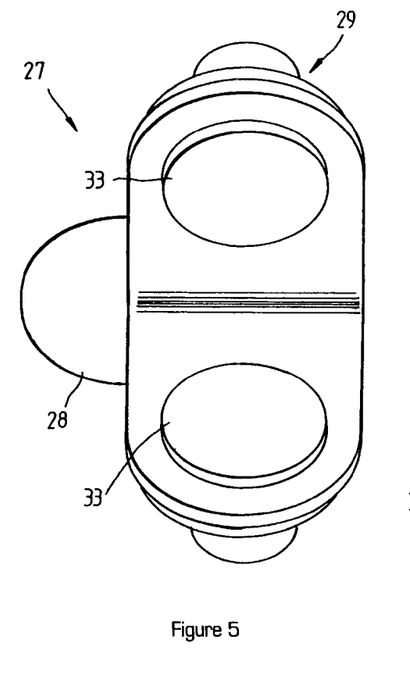
FIG. 5 is an end view of the apparatus shown in FIG. 4.

FIGS. 4 and 5 illustrate a further embodiment of cough inducer 27 which is similar in principle to the embodiment of FIGS. 1 to 3 including a handpiece comprising an elongated body 28 provided with an applicator head 29 at one end, the elongated body 28 comprising a gripping handle carrying an on-off switch 30. The applicator head 29 in this instance includes a pair of opposite arms 31 extending symmetrically of the body 28 and having outer faces defining a V-shaped concave recess 32 on its operative side extending through approximately 80 degrees to 100 degrees. Each arm 31 carries a piezoelectric transducer 33 and the transducers 33 thus have their active faces angled to each other at approximately 90 to 100 degrees to each other, the transducers 33 being arranged symmetrically relative to the body 28. The transducers 33 are also covered by a V-shaped flexible padding 34 of foam plastics material or the like. The transducers 33 may also be spring mounted by means of springs 35 to enable the transducers 33 to retract or extend from the arm portions 31 to fit a neck to which the inducer 27 is applied.

In this embodiment, a signal oscillator to actuate the transducers 33 is provided externally of the handpiece being connected to the transducers 33 via the switch 30 and a signal supply cable 36 connected to the body 28.

The inducer 27 is used in a similar manner to that described above with the applicator head 29 applied against the neck of a person or animal and a signal applied to the transducers 33 to cause ultrasonic vibrations to pass through the padding 34 to penetrate the neck and induce a coughing reflex.

Figure 6:
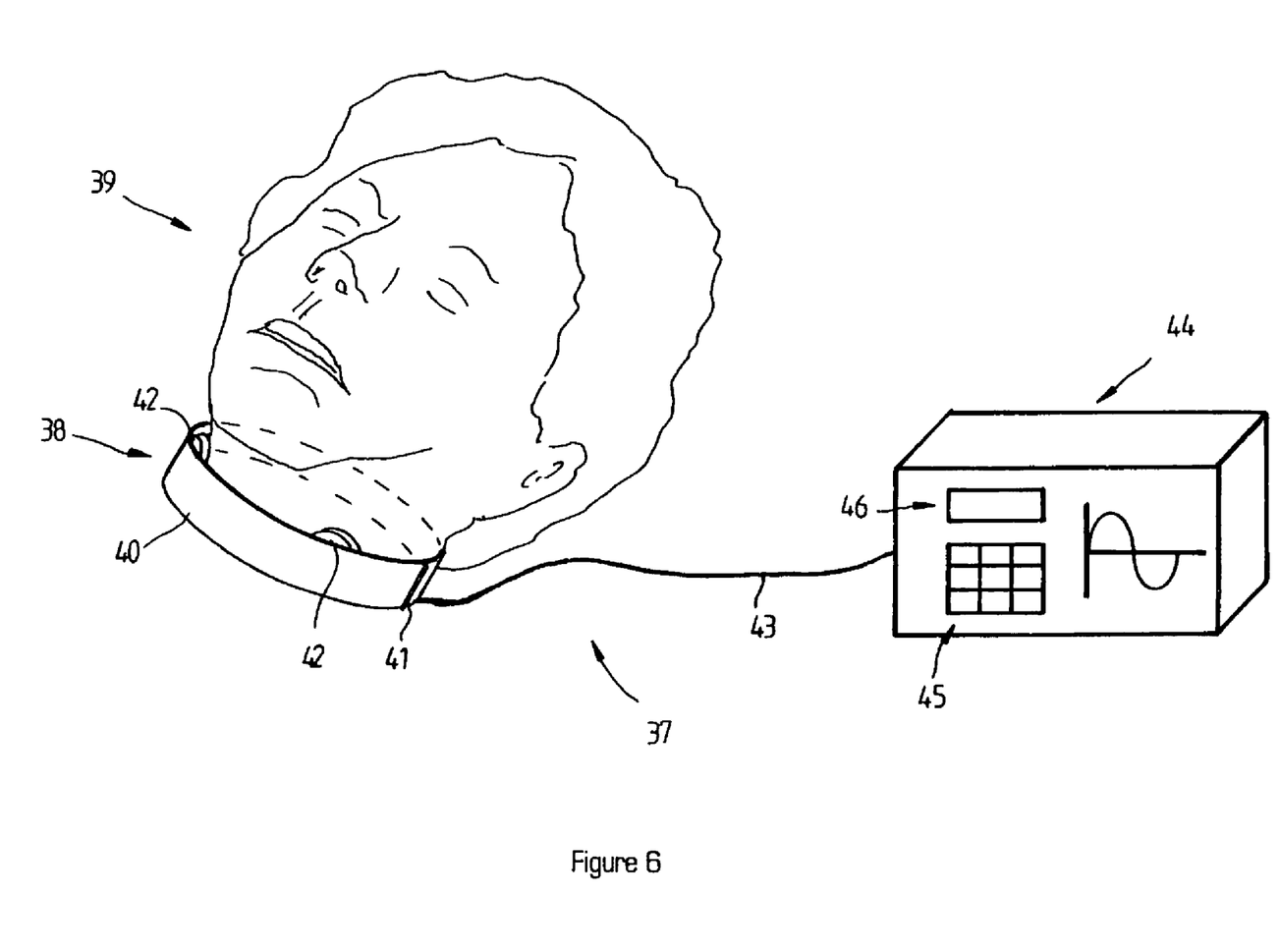
FIG. 6 illustrates an alternative embodiment of a coughing-reflex inducer apparatus according to another embodiment of the invention.

FIG. 6 illustrates an alternative embodiment of cough inducer 37 according to the invention including an applicator head 38 shown attached around the neck of a patient 39. The applicator head 38 is in the form of an annular collar 40, which is preferably moulded of polyurethane or similar material that provides optimum flexibility, strength and elasticity. The collar 40 can be split at 41 to enable it to be applied around the neck and then rejoined, the collar 40 carrying a pair of ultrasonic piezo-ceramic transducers 42 at spaced apart positions around the collar 40 so as to be angled typically at about 90 degrees to each other and when the collar 40 is applied to the neck, the transducers 42 are held snugly to the patients neck in the appropriate positions.

The piezo-ceramic transducers 42 are caused to vibrate by an applied ultrasonic signal that is delivered via a connecting lead 43 to the transducers 42 through the applicator head 38 from an oscillator housed in a housing 44 of polyurethane or other similar material so as to cause the transducers 42 to vibrate at an ultrasonic frequency. Preferably the housing 44 houses a printed circuit board and other electronic components that modulate the ultrasonic wave. In addition, the housing 44 includes a programmable controller having an external keypad 45 and display 46, which permits the application of the signal to be controlled as referred to below.

The applied electrical signal has parameters that are most efficacious in stimulating a cough reflex in the subject in terms of, but not limited to, frequency, intensity, wave shape and form, pulse width and pulse frequency. Furthermore, the rate and period at which these signals are delivered can be preprogrammed by the clinician via software and through input to the keypad 45 to deliver the therapeutic cough at clinically appropriate intervals for example at set or variable time intervals. For example, the clinician may choose to stimulate a cough every 10 minutes in the patient. Alternatively, the clinician can for example program three coughs, at intervals of one minute, every two hours, for two days. Similarly, the clinician will be able to use their clinical judgement to program any reasonable combination and timing of the therapeutic coughing.

Trials have been carried out to determine the efficacy of the method and apparatus of the invention and during the trials, ultrasonic stimuli was applied to the neck in two sets of eight frequencies between 20 KHz and 1350 KHz applied through a single transducer at 6 watts. These eight frequencies were chosen in random order and applied to a random side of the neck. The same eight frequencies were randomly repeated, this time at 10 watts. All stimuli were applied for 10 seconds, or until the subject was strongly coughing. In all cases during the study, the application of stimuli was double blinded. Thus neither the subject nor the investigator knew which frequency was being applied.

A second part of the study examined the efficacy of bilateral (a pair of transducers) versus unilateral application (a single transducer) of stimuli. During this phase, four stimuli were randomly applied at 4 watts, either bilateral, left, right or a repeat bilateral application. These stimuli were similarly repeated at 6 watts. As previously, both subject and investigator were blinded to whether the stimulation was unilateral or bilateral.

After each stimuli application, the subject was asked to rate the unpleasantness of the sensation and the investigator rated the cough response. The excursion of the chest and abdomen was also measured to record the breathing/coughing pattern.

The trials established that the lower frequency vibrations of the transducers (20 KHz-600 KHz) were more effective at cough stimulation than were the higher frequencies.

The trials further established that paired transducers were significantly more effective than a single transducer both at a lower intensity (4 watts) and a stronger intensity (6 watts). In all analyses, the paired transducers were approximately 150 percent more effective than were single transducers.

As with the single transducers, the unpleasantness of the sensation was also examined with the most unpleasant stimulus being with paired transducer at 6 watts producing midway between mild and moderate sensation.

It was concluded from the tests that paired transducers are more effective than the single transducer at stimulating a cough and this occurs with minimal increase in unpleasantness to the subject.

Further, the trials included a study to ensure that apparatus was safe to use and did not have any unwanted side effects. All vital signs of subjects (heart rate, blood pressure, oxygen saturation, respiratory rate, expiratory flow and local tissue observations) were recorded and tabulated and full statistical analysis of all vital signs for all patients revealed no significant changes as a result of the ultrasonic stimulus.

It will of course be realised that, while the foregoing has been given by way of illustrative example of the invention, all such and other modifications and variations thereto as would be apparent to persons skilled in the art are deemed to fall within the broad scope and ambit of the invention.

The invention claimed is:

1. Coughing reflex inducing apparatus for inducing a coughing reflex in a person or animal, said apparatus including:
   an applicator assembly, said applicator assembly comprising:
   a transducer support, said transducer support being of a curved or concave configuration on one side which is configured to accommodate the neck of the person or animal, and
   a pair of spaced apart ultrasonic transducers positioned at the ends of the curved or concave configuration of said transducer support, said transducers being angled towards each other; and
   an ultrasonic wave generator connected to said ultrasonic transducers for producing ultrasonic vibrations in said transducers of a frequency suitable for at least limited penetration of soft body tissue of the neck, the ultrasonic vibrations from the respective said ultrasonic transducers being applied in use to said spaced regions of the neck to stimulate the upper respiratory tract and cause a reflexive coughing response in said person or animal.

2. Apparatus as claimed in claim 1 wherein said ultrasonic transducers are angled to each other to transmit ultrasonic vibrations at approximately ninety degrees to each other.

3. Apparatus as claimed in claim 1 wherein said frequency of said ultrasonic vibrations is in the range of 20 KHz to 600 KHz.

4. Apparatus as claimed in claim 1 and including a main body comprising a gripping handle for said apparatus, said transducer support being provided at one end of said main body, said main body extending away from said transducer support from the side of said transducer support opposite said one side, said transducer support extending symmetrically to opposite sides of said main body.

5. Apparatus as claimed in claim 4 wherein said applicator assembly is detachably mounted to said main body to enable its interchange with further said applicator assemblies.

6. Apparatus as claimed in claim 5 wherein said transducer support has central attachment means for mounting said transducer support to said one end of said main body and wherein said transducers are arranged along said transducer support symmetrically on opposite sides of said attachment means.

7. Apparatus as claimed in claim 1 wherein said concavity of said transducer support is defined by a pair of opposite arms extending at substantially 90 degrees to each other whereby said transducers supported thereon are angled to each other at substantially 90 degrees.

8. Apparatus as claimed in claim 1 wherein said ultrasonic wave generator comprises an electrical oscillator producing a sine wave signal and wherein said transducers are adapted to produce mechanical vibrations in response to an electrical input from said oscillator.

9. Apparatus as claimed in claim 1 wherein said support comprises a flexible mount whereby said transducers are flexibly mounted relative to one another.

10. Apparatus as claimed in claim 1 wherein said transducers are mounted to said support by flexible mounting means whereby said transducers are flexibly mounted relative to one another, said flexible mounting means comprising spring or resilient means permitting limited extension and retraction of said transducers relative to said support.

11. Apparatus as claimed in claim 1 wherein said transducer support comprises an annular collar adapted to be applied to the neck to at least partially surround the neck.

12. Apparatus as claimed in claim 11 wherein said ultrasonic wave generator is external of said collar and is connectable to said transducers to cause ultrasonic vibration of said transducers.

13. Apparatus as claimed in claim 12 and including adjustable timing means for varying the time of application of the signals from said ultrasonic wave generator to said transducers.

14. A method of inducing a reflexive coughing response in a person or animal, said method comprising the steps of providing an ultrasonic apparatus having ultrasonic wave generation means and an applicator assembly comprising a pair of spaced apart ultrasonic transducers, operating said ultrasonic wave generation means to produce ultrasonic vibrations in said pair of ultrasonic transducers of a frequency suitable for at least limited penetration of the soft body tissue of the neck of a person or animal, said frequency being between 20 KHz and 600 KHz, and applying said applicator assembly to a selected region of the neck of a person or animal to cause said ultrasonic vibrations from said pair of ultrasonic transducers to penetrate at least to a limited extent the soft tissue portion of the neck and cause said reflexive coughing response.

15. A method as claimed in claim 14 wherein said ultrasonic transducers being angled towards each other and where said method comprises the step of applying said applicator assembly to the neck of said person or animal to cause ultrasonic vibrations from each said transducer of said applicator assembly to penetrate at least to a limited extent the soft tissue portion of the neck at spaced regions around the neck to cause said reflexive coughing response.

16. Cough inducing apparatus for inducing a coughing reflex in a person or animal, said apparatus including:
an elongated main body having a first end and a second end;
an applicator assembly comprising:
a transducer support having a concave side, said transducer support having spaced apart opposite free ends, the first end of said main body being connected to the transducer support on the side of said transducer opposite said concave side such that said main body extends from said first end away from said transducer support, said transducer support including respective support arms extending symmetrically to opposite sides of said main body from said first end of said main body to the opposite free ends of the transducer support respectively,
a first ultrasonic transducer supported on one transducer support arm and a second ultrasonic transducer supported on the other transducer support arm such that said transducers are arranged at spaced apart positions along said transducer support and are angled towards each other, said transducers being adapted to be located at spaced regions around the neck of the person or animal; and
an ultrasonic wave generator connectable to said ultrasonic transducers for producing ultrasonic vibrations in said transducers of a frequency suitable for at least limited penetration of soft body tissue of the neck and at said spaced regions of the neck whereby to stimulate the upper respiratory tract of said person or animal and cause a reflexive coughing response in said person or animal.

17. Cough inducing apparatus as claimed in claim 16 wherein said elongated main body comprises or is connected to a handle for gripping by a person.

18. Cough inducing apparatus as claimed in claim 16 wherein said transducer support arms comprise opposite arms and wherein said transducers are positioned on said arms such that vibrations therefrom are emitted at between 80 and 100 degrees to each other.

19. Cough inducing apparatus as claimed in claim 16 wherein said frequency of said ultrasonic vibrations is between 20 KHz and 600 KHz.

* * * * *